United States Patent [19]

Jones

[11] 4,250,043
[45] Feb. 10, 1981

[54] DETERGENT-COMPATIBLE ANTISTATIC COMPOSITIONS

[75] Inventor: Kenneth L. Jones, Cincinnati, Ohio

[73] Assignee: The Procter & Gamble Company, Cincinnati, Ohio

[21] Appl. No.: 59,007

[22] Filed: Jul. 19, 1979

[51] Int. Cl.³ .................. D06M 13/00; D06M 13/46; D06M 13/20; D06M 13/36

[52] U.S. Cl. ...................... 252/8.6; 8/115.6; 252/8.8; 252/8.9

[58] Field of Search .................. 252/8.6, 8.8; 8/115.6, 8/8.9

[56] References Cited

U.S. PATENT DOCUMENTS

| | | | |
|---|---|---|---|
| 3,896,033 | 7/1975 | Grimm | 252/8.6 |
| 3,936,537 | 2/1976 | Baskerville et al. | 427/242 |
| 3,951,879 | 4/1976 | Wixon | 252/8.8 |
| 3,959,155 | 5/1976 | Montgomery et al. | 252/8.8 |
| 4,018,688 | 4/1977 | Pracht et al. | 252/8.8 |
| 4,022,938 | 5/1977 | Zaki et al. | 252/8.8 |
| 4,098,937 | 7/1978 | Mizuno et al. | 428/247 |
| 4,118,525 | 10/1978 | Jones | 252/8.8 |
| 4,141,841 | 2/1979 | McDanald | 252/8.8 |

OTHER PUBLICATIONS

Derwent Publication 23372B/12 Abstract, Public Date 2-20-79, Anonymous "Fabric Conditioner Articles".

*Primary Examiner*—Joseph L. Schofer
*Assistant Examiner*—Herbert J. Lilling
*Attorney, Agent, or Firm*—Robert B. Aylor; Richard C. Witte; Thomas H. O'Flaherty

[57] ABSTRACT

Detergent-compatible antistatic compositions are described containing, as discrete particles, a water-soluble inorganic salt encapsulated in an organic dispersion inhibitor material. These compositions deliver through-the-wash static control benefits and are relatively inexpensive. Also described are detergent compositions containing the antistatic particles.

13 Claims, No Drawings

DETERGENT-COMPATIBLE ANTISTATIC COMPOSITIONS

TECHNICAL FIELD

This invention relates to compositions which provide through-the-wash static control in fabric laundering operations. More particularly, it relates to the provision of antistatic effects while simultaneously cleansing fabrics by means of conventional synthetic detergent surfactants and detergent builder materials.

BACKGROUND ART

It is desirable to include antistatic agents in detergent compositions to reduce the tendency of laundered fabrics to generate or retain static electricity when subjected to machine drying. Quaternary ammonium compounds have been widely used in detergent compositions for this purpose. However, these quaternary ammonium compounds are known to be generally incompatible with anionic surfactants commonly employed in laundering compositions. The anionic surfactants attack and inactivate the expensive cationic quaternary ammonium compounds in the wash-water environment. Techniques known in the art for preserving the antistatic properties of the cationic quaternary ammonium compounds focused on efforts to physically shield them from the hostile environment. For example, see U.S. Pat. No. 3,936,537, issued to Baskerville et al on Feb. 3, 1976, incorporated herein by reference, which discloses prilling of the quaternary ammonium compound with organic dispersion inhibitors; and U.S. Pat. No. 4,141,841, McDanald, issued Feb. 27, 1979, incorporated herein by reference, which discloses the agglomeration of the above-described prill with certain water-soluble neutral or alkaline salts, using organic agglomerating agents. Substitutes for these relatively expensive quaternary ammonium antistatic compounds would be useful.

Inorganic salts have been widely used as builders for detergent compositions to improve detergency levels of soaps and synthetic detergents, at least in part by sequestering calcium and/or magnesium ions in the wash water. It has also been recognized that various inorganic salts can be effective antistatic agents for fabrics. For example, U.S. Pat. No. 3,348,968, Hulbert et al, issued Oct. 24, 1967, teaches the application of aqueous solutions of certain inorganic salts to reduce static electricity in fabrics. However, inorganic salts have not been used in dry granular detergent compositions for antistatic purposes because they readily dissolve and disperse in the wash water and thus fail to deposit or become trapped on the laundered fabrics.

The present invention, by contrast, teaches the formulation of new discrete antistatic particles for use in granular detergent compositions. These antistatic particles deliver through-the-wash static control and are inexpensive compared to quaternary ammonium compounds. They are formed by encapsulating a water-soluble inorganic salt with an organic dispersion inhibitor material.

SUMMARY OF THE INVENTION

The present invention encompasses a particulate detergent additive product for preventing static buildup on textiles when applied thereto from a detergent wash liquor, said particulate product consisting essentially of:

(a) from about 80% to about 10% by weight of a water-soluble inorganic salt encapsulated in (b) from about 20% to about 90% by weight of a dispersion inhibitor, being a solid organic material having a solubility in water of 50 ppm max at 25° C. and a softening point in the range of 100° F. to 200° F., said material being selected from the group consisting of paraffinic waxes, cyclic and acyclic mono- and polyhydric alcohols, substituted and unsubstituted aliphatic carboxylic acids, esters of the foregoing alcohols and acids, $C_3$-$C_4$ alkylene oxide condensates of any of the foregoing alcohols and acids, and mixtures thereof, substantially all of the individual particles having a size within the range of 10 microns to 500 microns.

This particulate additive product can be incorporated into detergent compositions containing conventional detergent surfactants and builder materials. The particulate product can also be agglomerated with certain water-soluble neutral or alkaline salts prior to incorporation into detergent compositions, as described in U.S. Pat. No. 4,141,841, McDanald, for improved static control performance.

DISCLOSURE OF THE INVENTION

This invention comprises the discovery of new antistatic particles for use in detergent compositions. The antistatic particles herein are formed by encapsulating a water-soluble inorganic salt with an organic dispersion inhibitor material. Substantially all of the individual particles formed should have a size within the range of 10 microns to 500 microns, preferably from 25 microns to 250 microns, and more preferably from 50 microns to 100 microns.

While not intending to be limited by theory, it is believed that the relatively insoluble organic dispersion inhibitor material protects the water-soluble inorganic salt from extensive dissolution during the wash and rinse cycles. The antistatic particles are believed to remain intact in the wash, since the dispersion inhibitor material is relatively insoluble and has a melting point greater than that encountered in the washing process, and deposit or become trapped on the laundered fabrics. The antistatic particles are carried into the dryer where the dispersion inhibitor melts, spreading the particles over the drying fabrics, and freeing the salt to dissipate static electricity. It is surprising that the organic dispersion inhibitor material can protect these highly soluble inorganic salts sufficient to prevent their dissolution and dispersion in the wash water. Instead, discrete antistatic particles deposit on the laundered fabrics, allowing the salt to control static in the dryer.

The essential components in the particulate detergent additive product of the present invention are a water-soluble inorganic salt encapsulated in an organic dispersion inhibitor material. These two components are present in the particulate product of this invention at a weight ratio of salt to dispersion inhibitor of from 1:9 to 4:1, preferably from about 1:4 to 2:1. The encapsulated particulate product is preferably formed by spraying molten organic dispersion inhibitor material onto particles of the inorganic salt in a rotating mixing drum. Another preferred method of making these encapsulated antistatic particles involves admixing or slurrying solid particles of the inorganic salt with molten dispersion inhibitor material and cooling the mixture until the dispersion inhibitor solidifies. Suitable product within the scope of the present invention can also be formed by other methods which may only partially encapsulate the salt in the dispersion inhibitor material, such as those described in U.S. Pat. No. 3,936,537, Baskerville et al, which discloses methods of forming antistatic particles composed of an intimate mixture of quaternary ammonium compounds and organic dispersion inhibitors. Especially useful would be those methods wherein the salt and dispersion inhibitor materials are intimately mixed by dry mix addition followed by a mechanical process, such as milling, to form the particulates.

The inorganic salts for use herein should have a high conductivity to prevent the buildup of static electricity in the dryer. Thus, the salts should have one or more properties which permit them to effectively dissipate static electricity, such as a high solubility in water, high charge density, or a high ionic mobility. The salts preferably have a solubility in water of greater than about 0.5 moles per 100 ml of water at 100° C. For example, lithium chloride has a solubility in 100° C. water of about 2.7 moles/100 ml. Further, the present inorganic salts may be anhydrous or hydrated, so long as they are water-soluble.

Preferably, the inorganic salt is a water-soluble alkali metal, alkaline earth metal or ammonium salt; and more preferably is a water-soluble sodium, potassium, lithium, or ammonium salt. Preferred salts can also be selected from the group consisting of water-soluble halides, nitrates, nitrites, chlorates, acetates, sulfates, chromates, carbonates, sulfites, phosphates, arsenates, borates, and metal oxides and hydroxides; and more preferably, from the group consisting of water-soluble halides, nitrates, nitrites, chlorates and acetates. Especially preferred water-soluble inorganic salts are those which are alkali metal, alkaline earth metal, or ammonium halides, nitrates, chlorates, or acetates; and even more preferred are sodium, potassium, or lithium chlorides.

The organic dispersion inhibitor material for use herein has a solubility in water of 50 ppm max at 25° C. and a softening point in the range of 100° F. to 200° F., and is selected from the group consisting of paraffinic waxes, cyclic and acyclic mono- and polyhydric alcohols, substituted and unsubstituted aliphatic carboxylic acids, esters of the foregoing alcohols and acids, $C_3$–$C_4$ alkylene oxide condensates of any of the foregoing alcohols and acids, and mixtures thereof.

Preferred herein because of ready availability is tallow alcohol, but useful dispersion inhibitors include other fatty alcohols in the $C_{14}$–$C_{26}$ range such as myristyl alcohol, cetyl alcohol, stearyl alcohol, arachidyl alcohol, behenyl alcohol, and mixtures thereof.

Saturated fatty acids having 12 to 24 carbon atoms in the alkyl chain can be used such as: lauric acid, myristic acid, palmitic acid, stearic acid, arachidic acid, and behenic acid, as well as mixtures of these, particularly those derived from naturally occurring sources such as tallow, coconut, and marine oils.

Esters of the aliphatic alcohols and fatty acids are useful dispersion inhibitors, provided they have a total of more than 22 carbon atoms in the acid and alkyl radicals.

Long chain $C_{22}$–$C_{30}$ paraffinic hydrocarbon materials such as the saturated hydrocarbon octacosane having 28 carbon atoms can also be used.

Another preferred class of materials useful in the present invention are the water insoluble sorbitan esters which comprise the reaction product of $C_{12}$–$C_{26}$ fatty acyl halides or fatty acids and the complex mixtures of cyclic anhydrides of sorbitol collectively known as "sorbitan".

The sorbitan esters are, in turn, complex mixtures of mono, di, tri, and tetra ester forms, of which the tri and tetra are the least water-soluble and hence the most preferred for the purposes of the present invention. However, commercially available mixtures of the various forms are quite satisfactory provided that the mixture satisifies the water solubility and melting point range constraints for the organic dispersion inhibitor. Typical fatty acids that are suitable for the alkyl portion of the ester are palmitic, stearic, docosanoic, and behenic acids and mixtures of any of these. These sorbitan esters, particularly the tri and tetra esters, provide a degree of fabric softening in addition to their function as dispersion inhibitors. Minor proportions of unsaturated $C_{10}$–$C_{26}$ fatty acids, present in commercially available fatty acid mixtures such as coconut-, palm-, tallow-, and marine oil-derived acids are also acceptable. Another preferred group of materials are the $C_{20}$–$C_{26}$ mono- and di- ester forms which also provide a degree of fabric softening performance in addition to their function as dispersion inhibitors.

Preferred dispersion inhibitors are $C_{10}$–$C_{22}$ alkyl sorbitan esters, such as sorbitan trilaurate, sorbitan trimyristate, sorbitan tripalmitate, sorbitan tristearate, sorbitan tetralaurate, sorbitan tetramyristate, sorbitan tetrapalmitate, sorbitan tetrastearate, and mixtures thereof. Most preferably, the dispersion inhibitor is tallow alcohol. Suitable organic dispersion inhibitors for use in this invention are fully described in U.S. Pat. No. 3,936,537, Baskerville et al.

The particulate detergent additive product of this invention may be incorporated into conventional detergent compositions, such as those described in U.S. Pat. No. 3,936,537, Baskerville et al, from Column 11, line 3 through Column 21. Specifically, detergent compositions herein contain: from about 5% to 85%, preferably about 10% to 30% by weight of detergent surfactant selected from the group consisting of anionic, nonionic, ampholytic, and zwitterionic surfactants, and mixtures thereof; from about 5% to 75%, preferably about 10% to 50%, by weight of a detergent builder material; and from about 1% to 20%, preferably about 2% to 10%, by weight of the particulate detergent additive product of this application. As a preferred embodiment of the present invention, detergent compositions contain from about 10% to 50% by weight of a particulate detergent additive which is an agglomerate of from about 5% to 75% by weight of a water-soluble neutral or alkaline salt and from about 5% to about 75% by weight of the salt/dispersion inhibitor antistatic particles. This agglomerate delivers improved static control performance at reduced antistatic agent levels. Water-soluble neutral or alkaline salts, and their agglomeration with antistatic agents, are fully described in U.S. Pat. No. 4,141,841, McDanald.

Other ingredients which are conventionally used in detergent compositions can be included in the detergent compositions of the present invention. These components include detergency builders, such as those enumerated in the Baskerville et al patent from column 13, line 54 through column 16, line 17, as well as color speckles, bleaching agents and bleach activators, suds boosters or suds suppressors, anti-tarnish and anti-corrosion agents, soil suspending agents, soil release agents, dyes, fillers, optical brighteners, germicides, pH adjusting agents, alkalinity sources, hydrotropes, enzymes, enzyme-stabilizing agents, perfumes, alkyl polyethoxylate nonionic surfactants, and other optional detergent compounds.

As used herein, all percentages, parts and ratios given are "by weight", unless otherwise specified.

The following nonlimiting examples illustrate the additives and compositions of the present invention.

EXAMPLE I

The following detergent composition is produced.

| Ingredient | Base Granules Parts | Admix Parts | Finished Product 18.6% Admix |
|---|---|---|---|
| Sodium ($C_{13}$) linear alkylbenzene sulfonate ($C_{13}$ LAS) | 14.74 | — | 12.0 |
| $C_{12-13}$ (EO)$_{6.5}$* | 3.69 | — | 3.0 |
| Sodium silicate (2.0r) | 14.74 | — | 12.0 |
| Sodium tripolyphosphate | 24.32 | 24.5 | 24.4 |
| Sodium sulfate | 30.71 | — | 25.0 |
| Sodium toluene sulfonate | 1.23 | — | 1.0 |
| Tallow fatty acid | 0.61 | — | 0.5 |
| Brightener | 0.06 | — | 0.05 |
| Moisture | 6.00 | 12.6 | 7.2 |
| Perfume | 0.15 | — | 0.15 |
| Sodium chloride/tallow alcohol particles (4:3 ratio) | — | 37.6 | 7.0 |
| Sodium montmorillonite clay (ion exchange capacity about 63 meq/100 g, commercially available from Georgia Kaolin Co., USA, under the trade name BROCK) | — | 33.4 | 6.2 |
| Dextrin glue | — | 6.2 | 1.2 |
| Miscellaneous (dyes, etc.) | — | 1.8 | 0.3 |
| | 100.0 | 100.0 | 100.0 |

*Condensation product of $C_{12-13}$ alcohol with 6.5 moles of ethylene oxide, stripped to remove lower ethoxylate and non-ethoxylated fractions, commercially available as Neodol 23-6.5T, from Shell Chemical Corporation.

EXAMPLE II

The following detergent composition is produced.

| Ingredient | Base Granule Parts | Admix Parts | Finished Product Parts |
|---|---|---|---|
| Sodium ($C_{12}$) linear alkylbenzene sulfonate | 14.3 | — | 12.0 |
| $C_{12-13}$(EO)$_{6.5}$ | 3.6 | — | 3.0 |
| Sodium aluminosilicate (hydrated Zeolite A, particle diameter 1–10 microns) | 27.5 | — | 23.0 |
| Sodium silicate (2.0r) | 14.3 | — | 12.0 |
| Sodium sulfate | 22.3 | 24.6 | 22.7 |
| Sodium carbonate | 11.9 | — | 10.0 |
| Brightener | .06 | — | .05 |
| Moisture | 6.0 | — | 5.0 |
| Lithium chloride/tallow alcohol particles (1:1 ratio) | — | 43.4 | 7.0 |
| Sodium montmorillonite clay (ion exchange capacity about 63 meq/100 g, commercially available from Georgia Kaolin Co., USA, under the trade name BROCK) | — | 38.9 | 6.5 |
| Sodium tetraborate (anhydrous) | — | 11.8 | 2.0 |

EXAMPLE III

The following detergent composition is produced.

| | Parts |
|---|---|
| Base Detergent Granule | |
| Sodium ($C_{12}$) linear alkylbenzene sulfonate | 12.0 |
| Sodium ($C_{14-15}$) alkyl polyethoxylate (1.1) sulfate | 6.0 |
| Sodium silicate (2.0 ratio) | 11.5 |
| Tallow fatty acid | 0.5 |
| Sodium tripolyphosphate | 16.8 |
| Sodium sulfate | 16.5 |
| Moisture | 5.3 |
| TOTAL base detergent granule | 68.6 |
| Admix | |
| Sodium montmorillonite clay (ion exchange capacity about 63 meq/100 g, commercially available from Georgia Kaolin Co., USA, under the trade name BROCK) | 8.3 |
| Sodium tripolyphosphate | 6.6 |
| Potassium nitrate/tallow alcohol particles (1:1 ratio) | 10.0 |
| Miscellaneous (perfume, speckles, water and others) | 6.5 |
| TOTAL | 100.0 |

The compositions of Examples I, II and III deliver good cleaning and acceptable static control in laundered fabrics.

Acceptable static control in laundered fabrics is also obtained when the salts in the antistatic particles of the compositions of Examples I, II and III are replaced with other water-soluble inorganic salts, especially when the salt is a water-soluble alkali metal, alkaline earth metal or ammonium salt, or when the salt is selected from the group consisting of water-soluble halides, nitrates, nitrites, chlorates, acetates, sulfates, chromates, carbonates, sulfites, phosphates, arsenates, arsenites, borates, and metal oxides and hydroxides. Similar static control is also obtained when the tallow alcohol in the above compositions is replaced with the other organic dispersion inhibitor materials herein, especially with a $C_{10}$–$C_{22}$ alkyl sorbitan ester, such as sorbitan trilaurate, sorbitan trimyristate, sorbitan tripalmitate, sorbitan tristearate, sorbitan tetralaurate, sorbitan tetramyristate, sorbitan tetrapalmitate, sorbitan tetrastearate and mixtures thereof. Acceptable static control is also obtained when the weight ratio of the salt to the dispersion inhibitor in the above antistatic particles is anywhere from 1:9 to 4:1, and especially when the weight ratio is about 1:4, 1:3, 1:2, 1:1, or 2:1.

EXAMPLE IV

A standard mini-bundle of fabrics having the following composition was prepared.

| Composition of Standard Mini-bundle | | |
|---|---|---|
| Fabric Type | Number of Swatches | % of Total Bundle Weight |
| Cotton | 4 | 37 |
| Polycotton (65/35) | 2 | 14 |
| Nylon | 2 | 14 |
| Polyester (dacron) | 2 | 35 |
| | 10 | 100 |

The mini-bundle fabrics were washed for ten minutes with the indicated detergent composition, containing a base-granule composition admixed with a particulate anti-static additive product, in a miniature washer containing 1½ gallons of washing liquor at 105° F. and 7 gr/gal. artificial hardness (2 moles $Ca^{++}$:1 mole $Mg^{++}$). The swatches comprised 4% by weight of the washing liquor. After washing, the swatches were spun dry and rinsed with 1½ gallons of water, also at 105° F. and having similar 7 gr/gal. artificial hardness. Swatches were then dried in a miniature electric dryer. The fabrics were then measured for average volts per square yard, using a Faraday cage apparatus, and for number of clings. The results were as follows:

| Ingredient | Base Granule Composition | |
|---|---|---|
| | Composition A Parts | Composition B Parts |
| Soap | 0.5 | — |
| Sodium ($C_{11.8}$) linear alkylbenzene sulfonate | 12.0 | 10.0 |
| Sodium fatty alcohol ($C_{14-16}$) polyethoxylate ($EO_{2.25}$) sulfate | — | 11.0 |
| Sodium fatty alcohol ($C_{14-16}$) polyethoxylate ($EO_{1.0}$) sulfate | 6.0 | — |
| Sodium silicate (2.0r) | 12.0 | 12.0 |
| Sodium tripolyphosphate | 20.2 | 24.4 |
| Sodium sulfate | 20.0 | 35.2 |
| Tallow fatty acid | — | 0.25 |
| Sodium carboxymethyl-cellulose | — | 0.3 |
| Miscellaneous (includes brightener, perfume, etc.) | 0.7 | 0.7 |
| Moisture | 4.6 | 6.0 |
| | 76.0 | 99.9 |

| Antistatic Product | Other Wash-Added Ingredients* | Σ\|-V\|/ Sq. Yd. | R.H. | # Items Clinging |
|---|---|---|---|---|
| Group A | | | | |
| 4 parts ditallow dimethylammonium chloride/ 3 parts hydrogenated castor oil | 76 parts Comp. A 5 parts sodium tripolyphosphate speckles +12 parts sodium montmorillonite clay | 2.7 | 45 | 0 |
| 4 parts ditallow dimethylammonium chloride/ 2 parts hydrogenated castor oil | (same as above) | 1.7 | 45 | 0 |
| 4 parts ditallow dimethylammonium chloride/ 1 part hydrogenated castor oil | (same as above) | 4.5 | 45 | 0 |
| 4 parts ditallow dimethylammonium chloride/ 3 parts ethylene glycol distearate | 100 parts Comp. B | 1.0 | 27 | 0 |
| 4 parts ditallow dimethylammonium chloride/2 parts ethylene glycol distearate | 100 parts Comp. B | 2.2 | 27 | 0 |
| 4 parts ditallow dimethylammonium chloride/ 1 part ethylene glycol distearate | 100 parts Comp. B | 0.5 | 27 | 0 |
| Group B | | | | |
| 4 parts NaCl/ 3 parts tallow alcohol | 100 parts Comp. B | 3.1 | 42 | 0 |
| 4 parts KCl/ 3 parts tallow alcohol | 100 parts Comp. B | 3.6 | 48 | 0 |
| 4 parts $NH_4Cl$/ 9.4 parts tallow alcohol | 93 parts Comp. A | 3.8 | 49 | 0 |
| 5.4 parts $(NH_4)_2SO_4$/ 6 parts tallow alcohol | 93 parts Comp. A | 4.3 | 48 | 2 |
| 4 parts $MgCl_2$/3 parts tallow alcohol | 100 parts Comp. B | 8.7 | 44 | 5 |
| 4 parts $CaCl_2$/ 3 parts tallow alcohol | 100 parts Comp. B | 4.1 | 44 | 2 |
| 4 parts $Na_2SO_4$/ 3 parts tallow alcohol | 100 parts Comp. B | 6.8 | 42 | 2 |
| 4 parts $Al_2(SO_4)_3$ . 18 $H_2O$/ 3 parts palmitic acid | 100 parts Comp. B +10 parts sodium montmorillonite clay | 6.2 | 46 | 4 |

*100 parts = 1200 ppm in the washing machine.

These results demonstrate that particles of water-soluble inorganic salts encapsulated in organic dispersion inhibitor materials (Group B above) delivered through-the-wash static control which, in some cases, was equivalent to that obtained using the expensive quaternary ammonium antistatic particles (Group A above).

What is claimed is:

1. A particulate detergent additive product for preventing static buildup on textiles when applied thereto from a detergent wash liquor, said particulate product consisting essentially of:
   (a) from about 80% to about 10% by weight of a water-soluble inorganic salt encapsulated in
   (b) from about 20% to about 90% by weight of a dispersion inhibitor, being a solid organic material having a solubility in water of 50 ppm max at 25° C. and a softening point in the range of 100° F. to 200° F., said material being selected from the group consisting of paraffinic waxes, cyclic and acyclic mono- and polyhydric alcohols, substituted and unsubstituted aliphatic carboxylic acids, esters of the foregoing alcohols and acids, $C_3$-$C_4$ alkylene oxide condensates of any of the foregoing alcohols and acids, and mixtures thereof,
substantially all of the individual particles having a size within the range of 10 microns to 500 microns, said particulate detergent additive product being free of quaternary, ammonium, antistatic compounds.

2. A particulate detergent additive product according to claim 1 wherein the salt is an alkali metal, alkaline earth metal or ammonium salt.

3. A particulate detergent additive product according to claim 2 wherein the salt is a sodium, potassium, lithium or ammonium salt.

4. A particulate detergent additive product according to claim 1 wherein the salt is selected from the group consisting of halides, nitrates, nitrites, chlorates, acetates, sulfates, chromates, carbonates, sulfites, phosphates, arsenates, arsenites, borates, and metal oxides and hydroxides.

5. A particulate detergent additive product according to claim 4 wherein the salt is selected from the group consisting of halides, nitrates, nitrites, chlorates and acetates.

6. A particulate detergent additive product according to claim 1 wherein the salt is an alkali metal, alkaline earth metal, or ammonium halide, nitrate, nitrite, chlorate, or acetate.

7. A particulate detergent additive product according to claim 6 wherein the salt is sodium, potassium or lithium chloride.

8. A particulate detergent additive product according to claims 1, 6 or 7 wherein the dispersion inhibitor is tallow alcohol.

9. A particulate detergent additive product according to claim 8 wherein the weight ratio of salt to dispersion inhibitor is from about 1:4 to 2:1.

10. A detergent composition for preventing static buildup on textiles laundered therewith comprising:
   (a) from about 5% to about 85% by weight of a surfactant selected from the group consisting of anionic, nonionic, ampholytic and zwitterionic surfactants, and mixtures thereof;
   (b) from about 5% to about 75% by weight of a detergency builder material;
   (c) from about 1% to about 20% by weight of a particulate product consisting essentially of:
      (1) from about 80% to about 10% by weight of a water-soluble inorganic salt encapsulated in
      (2) from about 20% to about 90% by weight of a dispersion inhibitor, being a solid organic material having a solubility in water of 50 ppm max at 25° C. and a softening point in the range 100° F. to 200° F., said material being selected from the group consisting of paraffinic waxes, cyclic and acyclic mono-and polyhydric alcohols, substituted and unsubstituted aliphatic carboxylic acids, esters of the foregoing alcohols and acids, $C_3$-$C_4$ alkylene oxide condensates of any of the foregoing alcohols and acids, and mixtures thereof,
substantially all of the individual particles having a size within the range 10 microns to 500 microns, said particulate detergent additive product being free of quaternary, ammonium, antistatic compounds.

11. A detergent composition for preventing static buildup on textiles laundered therewith comprising:
   (a) from about 5% to about 85% by weight of surfactant selected from the group consisting of anionic, nonionic, ampholytic and zwitterionic surfactants, and mixtures thereof,
   (b) from about 5% to about 75% by weight of detergency builder material,
   (c) from about 10% to about 50% by weight of a detergent additive comprising an agglomerate of:
      (1) from about 5% to about 75% by weight of a water-soluble, neutral or alkaline salt, and
      (2) from about 5% to about 75% of a particulate product consisting essentially of:
         (i) from about 80% to about 10% by weight of a water-soluble inorganic salt encapsulated in
         (ii) from about 20% to about 90% by weight of a dispersion inhibitor, being a solid organic material having a solubility in water of 50 ppm maximum at 25° C., and a softening point in the range of 100° F. to 200° F., said material being selected from the group consisting of paraffinic waxes, cyclic and acyclic mono-and polyhydric alcohols, substituted and unsubstituted aliphatic carboxylic acids, esters of the foregoing alcohol and acids, $C_3$-$C_4$ alkylene oxide condensates of any of the foregoing alcohols and acids, and mixtures thereof,
substantially all of the individual particles (2) of the detergent additive having a size within the range of 10 microns to 500 microns, said particulate detergent additive product being free of quaternary, ammonium, antistatic compounds.

12. A detergent composition according to claims 10 or 11 wherein the salt is an alkali metal, alkaline earth metal or ammonium halide, nitrate, nitrite, chlorate or acetate.

13. A detergent composition according to claim 12 wherein the dispersion inhibitor is tallow alcohol.

* * * * *